(12) United States Patent
Suman et al.

(10) Patent No.: US 10,365,232 B2
(45) Date of Patent: Jul. 30, 2019

(54) HIGH ACCURACY OF RELATIVE DEFECT LOCATIONS FOR REPEATER ANALYSIS

(71) Applicant: KLA-Tencor Corporation, Milpitas, CA (US)

(72) Inventors: Shishir Suman, Gaya (IN); Kenong Wu, Davis, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/939,278

(22) Filed: Mar. 29, 2018

(65) Prior Publication Data

US 2018/0328860 A1 Nov. 15, 2018

Related U.S. Application Data

(60) Provisional application No. 62/520,893, filed on Jun. 16, 2017.

(51) Int. Cl.
*G01N 21/956* (2006.01)
*G01N 21/95* (2006.01)
*G01N 23/2251* (2018.01)
*G01N 21/88* (2006.01)

(52) U.S. Cl.
CPC ... *G01N 21/95607* (2013.01); *G01N 21/9501* (2013.01); *G01N 23/2251* (2013.01); *G01N 2021/8861* (2013.01); *G01N 2223/6116* (2013.01); *G01N 2223/646* (2013.01)

(58) Field of Classification Search
CPC ......... G01N 21/9501; G01N 21/95607; G01N 2223/6116; G01N 2223/646; G01N 23/2251

USPC ...................... 356/237.1–237.6, 239.1–239.8
See application file for complete search history.

(56) References Cited

U.S. PATENT DOCUMENTS

| 7,069,155 | B1 | 6/2006 | Phan et al. |
| 8,126,255 | B2 | 2/2012 | Bhaskar et al. |
| 8,664,594 | B1 | 4/2014 | Jiang et al. |
| 8,692,204 | B2 | 4/2014 | Kojima et al. |
| 8,698,093 | B1 | 4/2014 | Gubbens et al. |
| 8,716,662 | B1 | 5/2014 | MacDonald et al. |
| 9,222,895 | B2 | 12/2015 | Duffy et al. |
| 2006/0291714 | A1 | 12/2006 | Wu et al. |

(Continued)

OTHER PUBLICATIONS

International Search Report and Written Opinion for PCT/US2018/032587 dated Aug. 24, 2018.

*Primary Examiner* — Tri T Ton
(74) *Attorney, Agent, or Firm* — Ann Marie Mewherter

(57) ABSTRACT

Methods and systems for transforming positions of defects detected on a wafer are provided. One method includes aligning output of an inspection subsystem for a first frame in a first swath in a first die in a first instance of a multi-die reticle printed on the wafer to the output for corresponding frames, swaths, and dies in other reticle instances printed on the wafer. The method also includes determining different swath coordinate offsets for each of the frames, respectively, in the other reticle instances based on the swath coordinates of the output for the frames and the corresponding frames aligned thereto and applying one of the different swath coordinate offsets to the swath coordinates reported for the defects based on the other reticle instances in which they are detected thereby transforming the swath coordinates for the defects from swath coordinates in the other reticle instances to the first reticle instance.

24 Claims, 5 Drawing Sheets

(56) References Cited

U.S. PATENT DOCUMENTS

| | | |
|---|---|---|
| 2009/0016595 A1 | 1/2009 | Peterson et al. |
| 2009/0041332 A1 | 2/2009 | Bhaskar et al. |
| 2013/0064442 A1 | 3/2013 | Chang et al. |
| 2018/0053292 A1* | 2/2018 | Song .................. G06T 7/001 |

* cited by examiner

HIGH ACCURACY OF RELATIVE DEFECT LOCATIONS FOR REPEATER ANALYSIS

BACKGROUND OF THE INVENTION

1. Field of the Invention

This invention generally relates to methods and systems for determining relative defect locations with relatively high accuracy for repeater analysis.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

Some current inspection methods detect repeater defects on wafers to thereby detect defects on reticles. For example, a reticle is repeatedly printed on a wafer in different areas to thereby create multiple instances of the reticle printed on the wafer. As such, if a defect is detected repeatedly ("a repeater defect") at multiple locations on a wafer corresponding to the same location on a reticle, the defects may be caused by the reticle itself. Therefore, repeater defects may be analyzed to determine if they are caused by reticle defects, rather than some other cause. A single-die reticle is generally defined as a reticle that consists of only one die. A multi-die reticle is one that consists of multiple dies.

In general, repeater defect detection (RDD) is performed as a wafer post-processing (PP) operation. For example, the inspection tool may perform normal die-to-die defect detection (DD), and after all wafer defects are reported, the RDD may be performed in a post-processing step rather than in a different computer component when the wafer is being scanned. The repeater defects are defined as defects positioned at the same relative reticle location (within a certain tolerance) in several instances of the reticle printed on the wafer.

In some currently used repeater defect detection methods and systems, such as those performed for multi-die reticles that have been printed on wafers, defects are detected swath-by-swath and defect locations are reported relative to the die or reticle. Such methods and systems produce good defect locations within each swath because premap and run-time alignment (RTA) aligns the dies in the same swath or reticle row. However, there is not any mechanism to align reticle instances between swaths across reticle-rows. The repeater defect locations between swaths on different reticle instances can be as large as 2× of swath location accuracy, e.g., about 300 nm or about 10 pixels. Ideally, repeater tolerance should be set equal to or larger than 300 nm to find all repeater instances. A relatively large repeater tolerance causes more random defects to be detected as repeaters.

Accordingly, it would be advantageous to develop systems and/or methods for determining relative defect locations with relatively high accuracy for repeater analysis that do not have one or more of the disadvantages described above.

SUMMARY OF THE INVENTION

The following description of various embodiments is not to be construed in any way as limiting the subject matter of the appended claims.

One embodiment relates to a system configured to transform positions of defects detected on a wafer. The system includes an inspection subsystem that includes at least an energy source and a detector. The energy source is configured to generate energy that is directed to a wafer. The detector is configured to detect energy from the wafer and to generate output responsive to the detected energy. The output includes multiple swaths of frames of output for each of multiple dies on the wafer, and each of multiple instances of a reticle printed on the wafer includes at least two instances of the multiple dies.

The system also includes one or more computer subsystems configured for detecting defects on the wafer by applying a defect detection method to the output generated by the detector. For single-die reticles, repeater defects cannot be detected by any approach with die-to-die comparison because repeater defect signal is canceled out by such comparisons. A different approach can be used for defect detection for single-die reticles. This is not the subject of the embodiments described herein. For multi-die reticles, the repeater defects do not appear in immediate neighboring dies, so die-to-die comparison can be used. Positions of the defects are reported by the defect detection method in swath coordinates.

The one or more computer subsystems are also configured for aligning the output for a first of the frames in a first of the multiple swaths in a first of the multiple dies in a first of the multiple instances of the reticle printed on the wafer to the output for corresponding others of the frames in corresponding others of the multiple swaths in corresponding others of the multiple dies in others of the multiple instances of the reticle printed on the wafer. In addition, the one or more computer subsystems are configured for determining different swath coordinate offsets for each of the frames, respectively, in the others of the multiple instances of the reticle based on differences between swath coordinates of the output for the frames and swath coordinates of the output for the first of the frames aligned thereto in the aligning step. The one or more computer subsystems are further configured for applying one of the different swath coordinate offsets to the swath coordinates reported for the defects detected on the wafer, where which of the different swath coordinate offsets is applied to the swath coordinates reported for the defects is determined based on the others of the multiple instances of the reticle in which the defects were detected, thereby transforming the swath coordinates reported for the defects from swath coordinates in the others of the multiple instances of the reticle to swath coordinates in the first of the multiple instances of the reticle. The system may be further configured as described herein.

Another embodiment relates to a computer-implemented method for transforming positions of defects detected on a wafer. The method includes steps for each of the functions of the one or more computer subsystems described above. The steps of the method are performed by one or more computer subsystems coupled to an inspection subsystem configured as described above. The method may be performed as described further herein. In addition, the method may include any other step(s) of any other method(s) described herein. Furthermore, the method may be performed by any of the systems described herein.

An additional embodiment relates to a non-transitory computer-readable medium storing program instructions executable on a computer system for performing a computer-implemented method for transforming positions of defects detected on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Other objects and advantages of the invention will become apparent upon reading the following detailed description and upon reference to the accompanying drawings in which.

Figure 1:
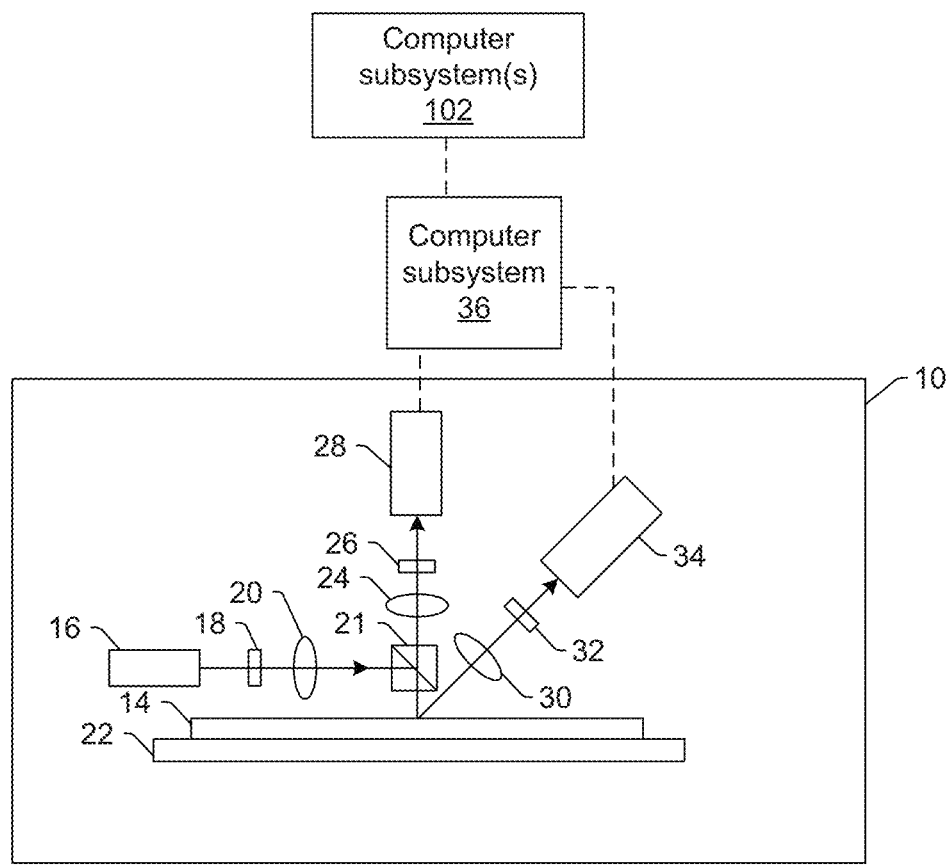
FIGS. 1 and 2 are schematic diagrams illustrating side views of embodiments of a system configured as described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to transform positions of defects detected on a wafer. The embodiments described herein are particularly suitable for detecting repeater defects on a wafer that are caused by a multi-die reticle printed on the wafer. For multi-die reticles, the die and reticle coordinate transformation is known and fixed for all die-rows. If a defect die location is determined, its reticle location can be calculated. In general, the embodiments described herein are configured for determining accurate (or substantially accurate) relative defect locations for repeater analysis. More particularly, the embodiments described herein generally transform defect locations from all reticle instances printed on a wafer to common coordinates during inspection and significantly increase relative defect location accuracy. The embodiments described herein can help to reduce the false repeater defect count for repeater analysis. The multi-die reticle can be any multi-die reticle known in the art. The wafer may include any wafer known in the art.

One embodiment of such a system is shown in FIG. 1. The system includes an inspection subsystem that includes at least an energy source and a detector. The energy source is configured to generate energy that is directed to a wafer. The detector is configured to detect energy from the wafer and to generate output responsive to the detected energy.

In one embodiment, the energy directed to the wafer includes light, and the energy detected from the wafer includes light. For example, in the embodiment of the system shown in FIG. 1, inspection subsystem 10 includes an illumination subsystem configured to direct light to wafer 14. The illumination subsystem includes at least one light source. For example, as shown in FIG. 1, the illumination subsystem includes light source 16. In one embodiment, the illumination subsystem is configured to direct the light to the wafer at one or more angles of incidence, which may include one or more oblique angles and/or one or more normal angles. For example, as shown in FIG. 1, light from light source 16 is directed through optical element 18 and then lens 20 to beam splitter 21, which directs the light to wafer 14 at a normal angle of incidence. The angle of incidence may include any suitable angle of incidence, which may vary depending on, for instance, characteristics of the wafer and the defects to be detected on the wafer.

The illumination subsystem may be configured to direct the light to the wafer at different angles of incidence at different times. For example, the inspection subsystem may be configured to alter one or more characteristics of one or more elements of the illumination subsystem such that the light can be directed to the wafer at an angle of incidence that is different than that shown in FIG. 1. In one such example, the inspection subsystem may be configured to move light source 16, optical element 18, and lens 20 such that the light is directed to the wafer at a different angle of incidence.

In some instances, the inspection subsystem may be configured to direct light to the wafer at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the wafer at the same time as the other light, one or more characteristics (e.g., wavelength, polarization, etc.) of the light directed to the wafer at different angles of incidence may be different such that light resulting from illumination of the wafer at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the wafer. Multiple illumination channels may be configured to direct light to the wafer at the same time or at different times (e.g., when different illumination channels are used to sequentially illuminate the wafer). In another instance, the same illumination channel may be configured to direct light to the wafer with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the wafer at different times. The illumination subsystem may have any other suitable configuration known in the art for directing light having different or the same characteristics to the wafer at different or the same angles of incidence sequentially or simultaneously.

In one embodiment, light source 16 may include a broadband plasma (BBP) light source. In this manner, the light generated by the light source and directed to the wafer may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the wafer. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for inspection.

The inspection subsystem may also include a scanning subsystem configured to cause the light to be scanned over the wafer. For example, the inspection subsystem may include stage 22 on which wafer 14 is disposed during inspection. The scanning subsystem may include any suitable mechanical and/or robotic assembly (that includes stage 22) that can be configured to move the wafer such that the light can be scanned over the wafer. In addition, or alternatively, the inspection subsystem may be configured such that one or more optical elements of the inspection subsystem perform some scanning of the light over the wafer. The light may be scanned over the wafer in any suitable fashion.

The inspection subsystem further includes one or more detection channels. At least one of the one or more detection channels includes a detector configured to detect light from the wafer due to illumination of the wafer by the inspection subsystem and to generate output responsive to the detected light. For example, the inspection subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the wafer. However, two or more of the detection channels may be configured to detect the same type of light from the wafer (e.g., specularly reflected light). Although FIG. 1 shows an embodiment of the inspection subsystem that includes two detection channels, the inspection subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the inspection subsystem may be signals or data, but not image signals or image data. In such instances, a computer subsystem such as computer subsystem 36 of the system may be configured to generate images of the wafer from the non-imaging output of the detectors. However, in other instances, the detectors may be configured as imaging detectors that are configured to generate imaging signals or image data. Therefore, the system may be configured to generate the output described herein in a number of ways.

It is noted that FIG. 1 is provided herein to generally illustrate a configuration of an inspection subsystem that may be included in the system embodiments described herein. Obviously, the inspection subsystem configuration described herein may be altered to optimize the performance of the system as is normally performed when designing a commercial inspection system. In addition, the systems described herein may be implemented using an existing inspection system (e.g., by adding functionality described herein to an existing inspection system) such as the 29xx/ 39xx and Puma 9xxx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Computer subsystem 36 of the system may be coupled to the detectors of the inspection subsystem in any suitable manner (e.g., via one or more transmission media, which may include "wired" and/or "wireless" transmission media) such that the computer subsystem can receive the output generated by the detectors during scanning of the wafer. Computer subsystem 36 may be configured to perform a number of functions using the output of the detectors as described herein and any other functions described further herein. This computer subsystem may be further configured as described herein.

This computer subsystem (as well as other computer subsystems described herein) may also be referred to herein as computer system(s). Each of the computer subsystem(s) or system(s) described herein may take various forms, including a personal computer system, image computer, embedded system, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as CPU and GPU. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Although the inspection subsystem is described above as being an optical or light-based inspection subsystem, the inspection subsystem may be an electron beam-based inspection subsystem. For example, in one embodiment, the energy directed to the wafer includes electrons, and the energy detected from the wafer includes electrons. In this manner, the energy source may be an electron beam source. In one such embodiment shown in FIG. 2, the inspection subsystem includes electron column 122, which is coupled to computer subsystem 124.

Figure 2:
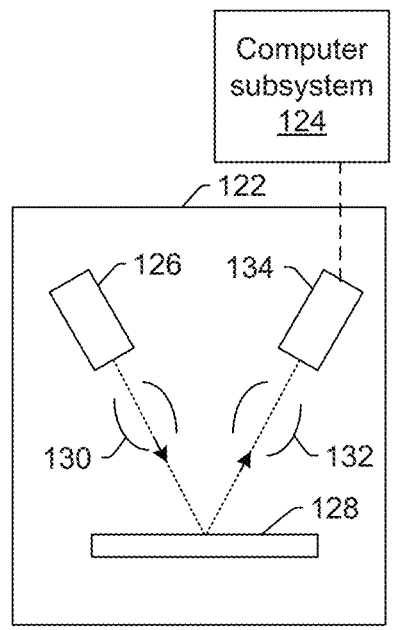

As also shown in FIG. 2, the electron column includes electron beam source 126 configured to generate electrons that are focused to wafer 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the wafer (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the wafer at an oblique angle of incidence and are scattered from the wafer at another oblique angle, it is to be understood that the electron beam may be directed to and scattered from the wafer at any suitable angles. In addition, the electron beam-based subsystem may be configured to use multiple modes to generate images of the wafer (e.g., with different illumination angles, collection angles, etc.). The multiple modes of the electron beam-based subsystem may be different in any image generation parameters of the subsystem.

Computer subsystem 124 may be coupled to detector 134 as described above. The detector may detect electrons returned from the surface of the wafer thereby forming electron beam images of the wafer. The electron beam images may include any suitable electron beam images. Computer subsystem 124 may be configured to perform any of the functions described herein using the output of the detector and/or the electron beam images. Computer subsystem 124 may be configured to perform any additional step(s) described herein. A system that includes the inspection subsystem shown in FIG. 2 may be further configured as described herein.

It is noted that FIG. 2 is provided herein to generally illustrate a configuration of an electron beam-based inspection subsystem that may be included in the embodiments described herein. As with the optical inspection subsystem described above, the electron beam-based inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the eSxxx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Although the inspection subsystem is described above as being a light-based or electron beam-based inspection subsystem, the inspection subsystem may be an ion beam-based inspection subsystem. Such an inspection subsystem may be configured as shown in FIG. 2 except that the electron beam source may be replaced with any suitable ion beam source known in the art. In addition, the inspection subsystem may be any other suitable ion beam-based subsystem such as those included in commercially available focused ion beam (FIB) systems, helium ion microscopy (HIM) systems, and secondary ion mass spectroscopy (SIMS) systems.

As noted above, the optical and electron beam inspection subsystems may be configured for directing energy (e.g., light, electrons) to and/or scanning energy over a physical version of the wafer thereby generating actual (i.e., not simulated) output and/or images for the physical version of the wafer. In this manner, the optical and electron beam inspection subsystems may be configured as "actual" tools, rather than "virtual" tools. Computer subsystem(s) 102 shown in FIG. 1 may, however, include one or more "virtual" systems (not shown) that are configured for performing one or more functions using at least some of the actual optical images and/or the actual electron beam images generated for the wafer, which may include any of the one or more functions described further herein.

The one or more virtual systems are not capable of having the wafer disposed therein. In particular, the virtual system(s) are not part of optical inspection subsystem 10 or electron beam inspection subsystem 122 and do not have any capability for handling the physical version of the wafer. In other words, in a system configured as a virtual system, the output of its one or more "detectors" may be output that was previously generated by one or more detectors of an actual inspection subsystem and that is stored in the virtual system, and during the "imaging and/or scanning," the virtual system may replay the stored output as though the wafer is being imaged and/or scanned. In this manner, imaging and/or scanning the wafer with a virtual system may appear to be the same as though a physical wafer is being imaged and/or scanned with an actual system, while, in reality, the "imaging and/or scanning" involves simply replaying output for the wafer in the same manner as the wafer may be imaged and/or scanned.

Systems and methods configured as "virtual" inspection systems are described in commonly assigned U.S. Pat. No. 8,126,255 issued on Feb. 28, 2012 to Bhaskar et al. and U.S. Pat. No. 9,222,895 issued on Dec. 29, 2015 to Duffy et al., both of which are incorporated by reference as if fully set forth herein. The embodiments described herein may be further configured as described in these patents. For example, the one or more computer subsystems described herein may be further configured as described in these patents.

The inspection subsystems described herein may be configured to generate output for the wafer with multiple modes or "different modalities." In general, a "mode" or "modality" (as those terms are used interchangeably herein) of an inspection subsystem can be defined by the values of parameters of the inspection subsystem used for generating output and/or images for a wafer. Therefore, modes that are different may be different in the values for at least one of the parameters of the inspection subsystem. In this manner, in some embodiments, the optical images include images generated by the optical inspection subsystem with two or more different values of a parameter of the optical inspection subsystem. For example, in one embodiment of an optical inspection subsystem, at least one of the multiple modes uses at least one wavelength of the light for illumination that is different from at least one wavelength of the light for illumination used for at least one other of the multiple modes. The modes may be different in the illumination wavelength as described further herein (e.g., by using different light sources, different spectral filters, etc.) for different modes. In another embodiment, at least one of the multiple modes uses an illumination channel of the optical inspection subsystem that is different from an illumination channel of the optical inspection subsystem used for at least one other of the multiple modes. For example, as noted above, the optical inspection subsystem may include more than one illumination channel. As such, different illumination channels may be used for different modes.

In a similar manner, the electron beam images may include images generated by the electron beam inspection subsystem with two or more different values of a parameter of the electron beam inspection subsystem. For example, the electron beam inspection subsystem may be configured to generate output for the wafer with multiple modes or "different modalities." The multiple modes or different modalities of the electron beam inspection subsystem can be defined by the values of parameters of the electron beam inspection subsystem used for generating output and/or images for a wafer. Therefore, modes that are different may be different in the values for at least one of the electron beam parameters of the inspection subsystem. For example, in one embodiment of an electron beam inspection subsystem, at least one of the multiple modes uses at least one angle of incidence for illumination that is different from at least one angle of incidence of the illumination used for at least one other of the multiple modes.

The output of the detector generated for the wafer includes multiple swaths of frames of output for each of multiple dies on the wafer, and each of multiple instances of a reticle printed on the wafer includes at least two instances of the multiple dies. For example, regardless of whether the detector(s) of the inspection subsystem produce signals and/or images, a "frame" may be generally defined as a relatively small portion of output (e.g., signals or image portions (e.g., pixels)) generated by an inspection subsystem that can be collectively processed as a unit by the system. Therefore, a "frame" of output can vary depending on the inspection subsystem configuration as well as the configuration of any components included in the system for handling and/or processing of the output generated by the inspection subsystem. A swath or a sub-swath of output generated for a wafer may be divided into multiple frames such that data handling and processing of the frames can be performed much more easily than if the entire swath or subswath of output is processed simultaneously. In addition, inspection generally divides a die or a reticle instance printed on a wafer into multiple swaths vertically as shown in figures described further herein.

The one or more computer subsystems are configured for detecting defects on the wafer by applying a defect detection method to the output generated by the detector. The defect detection method may be applied to the output in any suitable manner, and the defect detection method may include any suitable defect detection method known in the art. The defect detection method may include, for example, comparing the output to a threshold (a defect detection threshold) and the output that has one or more values above the threshold is determined to correspond to defects while the output that does not have one or more values above the threshold is not determined to correspond to defects. Applying the defect detection method to the output may also include applying any another defect detection method and/or algorithm to the output.

Positions of the defects are reported by the defect detection method in swath coordinates. For example, the defect detection method may generate results of applying the defect detection method to the output. The results may include at least a position of each defect and any other suitable information such as a defect ID, defect information (e.g., size) determined by the defect detection method, and the like. The defect detection method may be configured such that the defect positions are reported in swath coordinates. In other words, the defect positions that are reported for the defects may be in-swath positions or swath relative positions. In one such example, the swath coordinates for the defects may be determined relative to an origin (or other reference point) of the swath in which they were detected. In a particular example, each swath image can be viewed as a normal image. The top left corner of the normal image can be used as the origin of the swath in one such example. The swath coordinates of the defects may then be determined with respect to the top left corner of the swath. In this manner, the swath coordinates of the defects are determined with respect to the swath in which they are detected but are not determined with respect to the wafer being inspected. Locations of defects of a repeater may be different in different swaths because swath offsets to the wafer are different due to stage uncertainty. The embodiments described herein can effectively eliminate those differences as described further herein.

The one or more computer subsystems are configured for aligning the output for a first of the frames in a first of the multiple swaths in a first of the multiple dies in a first of the multiple instances of the reticle printed on the wafer to the output for corresponding others of the frames in corresponding others of the multiple swaths in corresponding others of the multiple dies in others of the multiple instances of the reticle printed on the wafer. In this manner, the output for corresponding frames of corresponding swaths in corresponding dies in different reticle instances printed on the wafer may be aligned to each other. In other words, the output for the first frame of the first swath of the first of the multiple dies in the first of the multiple instances of the reticle printed on the wafer may be aligned to the output for the corresponding frames of the corresponding swaths of the corresponding dies in other reticle instances printed on the wafer.

Aligning the output in one frame to its corresponding output in another frame as described above may be performed in any suitable manner. For example, in one embodiment, the aligning includes target-based alignment of the output for the first of the frames to the output for the corresponding others of the frames. In one such example, the aligning may be performed using alignment target(s) in the first frame (which may be selected as described further herein) and corresponding alignment sites in corresponding frames, and aligning the output for the alignment sites to the output generated for the alignment target may include pattern matching, matching one or more characteristics (e.g., a centroid, pattern edges, etc.) of the different output, etc. In other words, the embodiments described herein are not limited in the aligning that may be performed for the alignment sites and targets.

In another embodiment, the aligning includes feature-based alignment of the output for the first of the frames to the output for the corresponding others of the frames. The features that are used for this alignment may include patterned features in a design for the wafer, patterned features in images generated for the wafer by the inspection subsystem (which may or may not correspond to features on the wafer), features of patterns on the wafer such as edges, centroids, corners, structures, etc. of the patterns, and the like. Such alignment may be performed in any suitable manner. For example, such aligning may include feature matching (e.g., edge matching), which may be performed in any suitable manner known in the art.

In an additional embodiment, the aligning includes normalized cross correlation (NCC)-based alignment of the output for the first of the frames to the output for the corresponding others of the frames. The aligning may be performed using any suitable NCC method and/or algorithm known in the art. In a further embodiment, the aligning includes Fast Fourier transform (FFT)-based alignment of the output for the first of the frames to the output for the corresponding others of the frames. The aligning may be performed using any suitable FFT method and/or algorithm known in the art. In some embodiments, the aligning includes sum of squared difference (SSD)-based alignment of the output for the first of the frames to the output for the corresponding others of the frames. The aligning may be performed using any suitable SSD method and/or algorithm known in the art.

The one or more computer subsystems are further configured for determining different swath coordinate offsets for each of the frames, respectively, in the others of the multiple instances of the reticle based on differences between swath coordinates of the output for the frames and swath coordinates of the output for the first of the frames aligned thereto in the aligning step. In this manner, a swath coordinate offset may be separately and independently determined for each frame and each swath in each of the dies in each of the instances of the reticle printed on the wafer with respect to its corresponding frame. The swath coordinate offsets may be determined in any suitable manner based on the output in the frames that is aligned to the output for the first frame and their corresponding swath coordinates, respectively. The swath coordinate offsets may have any suitable format (e.g., a function or formula). In addition, information for the swath coordinate offsets may be stored in any suitable storage media described herein. Furthermore, the swath coordinate offsets may be determined in one only direction (e.g., the x or the y direction) or in two directions (e.g., the x and y directions). Moreover, the swath coordinate offsets may be determined using swath coordinates having any suitable format (e.g., polar and Cartesian coordinates).

The one or more computer subsystems are also configured for applying one of the different swath coordinate offsets to the swath coordinates reported for the defects detected on the wafer, where which of the different swath coordinate offsets is applied to the swath coordinates reported for the defects is determined based on the others of the multiple instances of the reticle in which the defects were detected, thereby transforming the swath coordinates reported for the defects from swath coordinates in the others of the multiple instances of the reticle to swath coordinates in the first of the multiple instances of the reticle. The frame, swath, die, and reticle instance in which a defect is detected may be determined based on the swath coordinates determined by the defect detection method for the defect. Based on the frame, swath, die, and printed reticle instance in which a defect is detected, the corresponding swath coordinate offset may be determined (because it is known which swath coordinate offset was determined for which frame, swath, die, and reticle instance and it is known which reticle instance each defect was detected in, that knowledge can be used to determine the appropriate swath coordinate offset based on the swath coordinates of the defects). That identified swath coordinate offset may then be applied to the swath coordinates determined for the defect thereby transforming the swath coordinates of the defect from the swath coordinates in the reticle instance in which it was detected to the swath coordinates in the first reticle instance. This swath coordinate transform process may be separately and independently performed for each defect detected on the wafer (or as many of the detected defects as desired). The swath coordinate offsets may be applied to the swath coordinates reported for the defects in any suitable manner.

Figure 4:
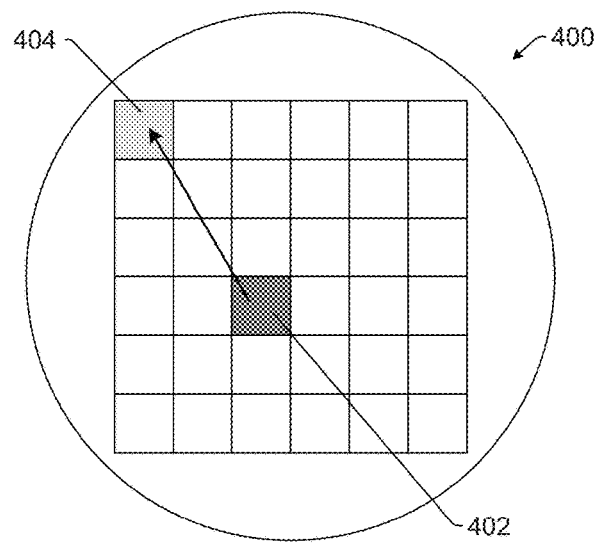
FIG. 4 is a schematic diagram illustrating a plan view of one example of instances of a reticle printed on a wafer and one embodiment of defect coordinate translation of individual instances of the reticle printed on the wafer to a first instance of the reticle printed on the wafer.

FIG. 4 illustrates the general concept of the transforming step described above. In particular, FIG. 4 shows the defect swath coordinate translation of individual reticle instances to a first inspected reticle instance. In this instance, wafer 400 includes a number of reticle instances formed thereon, and which include reticle instances 402 and 404. In the example shown in FIG. 4, reticle instance 404 may be used as the first inspected reticle instance, and locations of defects detected in reticle instance 402 may transformed to swath coordinates of reticle instance 404. In particular, as described above, the applying step maps defect locations into the swath coordinates of the first reticle instance by applying a swath coordinate transformation between the first and other reticle instances on the wafer. All defect locations transformed as described herein into the first reticle instance/swath coordinates are substantially accurate. As such, defects for each repeater are much closer than currently used inspection performed without this feature. In particular, in currently used inspection, since the swaths are not registered or aligned to each other, defects of one repeater can be relatively far from each other on a reticle stack. In contrast, in the embodiments described herein, all other reticle instances are registered to the first reticle instance and then defect locations from the other reticle instances are accurately mapped to the first reticle instance. Since the mapping is substantially accurate, defects of one repeater are mapped to the first reticle instance and are substantially close to one another.

Although one particular reticle instance (reticle instance 404) is shown in FIG. 4 (and other figures described herein) as being used as the first of the multiple reticle instances, the reticle instance that is used as the first of the multiple reticle instances may be different from that shown herein. In general, any reticle instance on the wafer that is scanned by the inspection subsystem (thereby generating output for the reticle instance) may be used as the first of the multiple reticle instances. In some instances, it may be practical to use the first reticle instance that is scanned as the first of the multiple reticle instances. However, any appropriate reticle instance may be used as the first reticle instance for the embodiments described herein.

In this manner, the embodiments described herein determine relative defect positions (or relative defect locations) with substantially high accuracy. As further described herein, the defect positions are transformed from swath coordinates of one reticle instance to swath coordinates of another reticle instance. Therefore, the relative defect positions are determined herein with respect to different swaths in one reticle instance. As such, the relative defect positions determined as described herein are different from absolute defect positions, which are generally defined as the defect positions relative to the wafer coordinates. In this manner, the relative defect location accuracy of the embodiments described herein is the accuracy relative to swath coordinates.

In one embodiment, the one or more computer subsystems are configured for performing the aligning, determining, and applying steps described above without design information for devices being formed on the wafer. For example, the embodiments described herein improve defect location accuracy relative to a specific reticle instance (the first reticle instance) and swath without design information for any multi-die reticle inspection. With respect to a multi-die reticle, a reticle is a mask. A die is a chip. If a mask includes one chip, it is a single die reticle. If a mask includes multiple chips, e.g., 3 chips, it is a multi-die reticle.

In another embodiment, the one or more computer subsystems are not configured to perform any steps using design information for devices being formed on the wafer. For example, as described above, the aligning, determining, and applying steps are performed without design information in one embodiment. In addition, no other of the steps described herein may be performed using design information. Therefore, the embodiments described herein can be performed regardless of whether or not design information is available for use in the systems and methods described herein.

In one embodiment, the wafer is printed with a multi-die reticle prior to the detecting. For example, the embodiments described herein may be used for detecting defects on multi-die reticles by detecting defects on wafers that were printed with the multi-die reticles and then determining which of the defects detected on the wafers are due to the multi-die reticles. Determining which of the defects detected on the wafers are due to the multi-die reticles may be performed by identifying repeating defects or "repeaters" on the wafers. In this manner, the defects detected on the wafers that are due to multi-die reticles used to print the wafers may be identified by repeater analysis, which may be performed as described further herein.

In some embodiments, the one or more computer subsystems are configured for determining if the defects are repeater defects based on the transformed swath coordinates for the defects. In this manner, the embodiments described herein may be configured to perform repeater analysis to determine which of the defects are repeaters. Repeaters are generally defined as a set of defects (e.g., two or more) that appear at the "same" reticle instance coordinates (where reticle instance coordinates can be considered to be the "same" if they are exactly the same or the same within some predetermined allowable tolerance). In addition, defects of a repeater are located on the same corresponding swaths (the same swath in multiple reticle instances) in fixed swath scanning. (In fixed swath scanning, a reticle instance image is acquired by a scan of multiple sub-die images or swath images. On a wafer, there are many die rows. Locations of corresponding swath images are the same for each die row. In other words, each die row is scanned with the same swath layout.) Repeater analysis is performed to find repeaters from all detected events.

As described further herein, by transforming the defect positions from swath coordinates in the reticle instances in which the defects were detected to swath coordinates of only one of the reticle instances on the wafer, the defect locations relative to a specific reticle instance and swath can be determined with substantially high accuracy. If defect locations relative to the swath in which they are located are more accurate, repeater analysis can use a smaller repeater tolerance and can thereby produce fewer false repeaters and reduce the repeater detection time. As such, the embodiments described herein allow the repeater search area to be reduced by 100× to 10,000× (or repeater tolerance by 10×, 10 pixels to 1 pixel for 100× area reduction, 10 pixels to 0.1 pixel for 10,000× area reduction) in repeater analysis. "Repeater tolerance" as that term is used herein is defined as the radius centered at a defect location. Repeater search range would be [−radius, +radius] approximately. The search area is the square of radius times π. The smallest search range in pixels is from [−0.1, 0.1] to [−1, 1] depending on the number of alignment targets that can be identified (or the accuracy of alignment that is performed in the aligning step). The smallest search area is from 0.0314 pixel squared to 3.14 pixel squared compared to 314 pixel squared. Reducing the repeater search area in this manner will potentially reduce false repeaters significantly.

Figure 3:
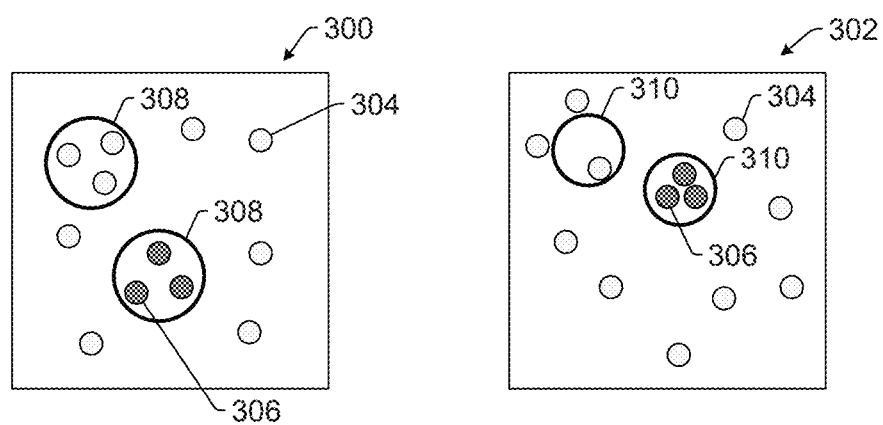
FIG. 3 is a schematic diagram illustrating a reticle stack view of examples of different repeater defect detection results generated for defects whose defect positions were determined with different defect location accuracies.

FIG. 3 illustrates how reducing the repeater search area will reduce false repeater detection. In general, as described with respect to this figure, there is a relationship between defect location accuracy, repeater tolerance, and false repeater detection, and the relative defect location accuracy has an impact on repeater detection. A repeater tolerance is a user-defined parameter which determines the repeater search area. A reticle stack is a view of defects on a number of aligned reticle instances superimposed together. All defects within a repeater search area on a reticle stack are considered as repeater defects belonging to a unique repeater. Unique repeaters are distinguished by their reticle coordinates. In one such example, a repeater defect detection algorithm may determine that if defects are detected in at least three reticle instances within a repeater search area, those three defects may be identified as repeaters.

In reticle stack view 300 shown in FIG. 3, defects 304 and 306 are shown. Defects 304 are multiple instances of nuisance defects, and defects 306 are multiple instances of defects of interest (DOIs). In particular, defects 304, shown by the lighter shading in FIG. 3, are known to be non-repeating defects and defects 306, shown by the darker shading in FIG. 3, are known to be repeating defects. The defects shown in FIG. 3 are not meant to show any actual defects detected on any actual wafer. Instead, these defects are merely shown in FIG. 3 to promote understanding of the embodiments described herein.

Reticle stack view 300 can be generated in any suitable manner, for instance, by overlaying information for defects detected in multiple reticle instances printed on a wafer. The information that is overlaid may include locations at which the defects were located, and the defects may be indicated at their locations in the reticle stack view by some symbol such as the shaded circles shown in FIG. 3. In this manner, defects that have spatial coincidence with each other in multiple reticle instances can be identified in the reticle stack view. In other words, defects that are detected at the same or substantially the same locations in the multiple reticle instances can be identified in the reticle stack view.

The repeater search area may be set based on the relative defect location accuracy of the defects being analyzed for repeaters. In particular, a larger repeater search area may be used when the relative defect location accuracy is lower, and a smaller repeater search area may be used when the relative defect location accuracy is higher. In this manner, the repeater search area may be different based on relative defect location accuracy so that repeaters can be identified regardless of the accuracy with which the locations have been determined. As shown in FIG. 3, if repeater search area 308 is set large enough so that it correctly identifies defects 306 as repeaters, the same repeater search area will also incorrectly identify some of defects 304 as repeaters. In this manner, due to relatively poor relative defect location accuracy of the defects detected in reticle stack view 300, a larger repeater tolerance is used and a false repeater is detected.

However, if the defect relative location accuracy is higher, the repeater defects are spatially closer and non-repeater defects are still distributed randomly. The repeater search area can be reduced while still correctly identifying repeating defects as such, then the number of non-repeating defects that are incorrectly identified as repeaters can be reduced. For instance, as shown in reticle stack view 302, which can be generated as described above, defects 304 and 306 are shown. As with reticle stack view 300, in reticle stack view 302, defects 304 are known to be non-repeating defects, and defects 306 are known to be repeating defects. When defect location accuracy is higher, then a smaller repeater search area can be used for repeater analysis of the reticle stack view. If repeater search area 310 having a smaller area than repeater search area 308 is able to be used in reticle stack view 302 because the relative defect locations were determined with greater accuracy as described herein, then defects 306 can be correctly identified as repeating defects without incorrectly identifying any of defects 304 as repeating defects. For example, as shown in FIG. 3, even the three most closely spaced of defects 304 are not all within repeater search area 310 and thus will not be identified as repeater defects. In this manner, by reducing the repeater search area, the number of defects that are incorrectly determined to be repeaters can be reduced.

In contrast to the embodiments described herein, the currently used methods and systems for inspection of wafers printed with multi-die reticles is to detect defects swath-by-swath and report defect locations relative to the wafer. This approach produces good defect locations on each swath because premap and run-time alignment (RTA) align reticle instances in the same swath or reticle row. However, there is not any mechanism to align reticle instances between swaths across reticle rows. The repeater defect locations between swaths on different reticle instances can be as large as 2× of swath location accuracy, e.g., about 300 nm or about 10 pixels. Ideally, in such situations, repeater tolerance should be set to equal to or larger than 300 nm to find all repeater instances. However, such a large repeater tolerance causes more random defects to be detected as repeaters.

As described further herein, the embodiments described herein determine relative defect positions or locations with substantially high accuracy. In contrast, absolute defect location accuracy or defect location accuracy (DLA), as that term is commonly used in the art, is the accuracy relative to the wafer coordinates. However, absolute DLA is not necessary and defect location accuracy relative to a common reticle-swath coordinate is sufficient for repeater analysis. More random events can be removed (i.e., eliminated as being not repeater defects) if defect locations are more accurate in a reticle stack where reticle location relative to the wafer are not considered. If defect locations relative to their reticle instance coordinates are more accurate, repeater analysis can use a smaller repeater tolerance and produces fewer false repeaters.

It is also noted that the embodiments described herein focus on methods and systems that detect defects with substantially high relative location accuracy. Repeater analysis may or may not be performed by the embodiments described herein. For example, the substantially high relative location accuracy of the defect positions determined by the embodiments described herein provide advantages for repeater detection regardless of how it is performed. In other words, the embodiments described herein provide substantially accurate defect relative positions that can then be used in any repeater detection process. In this manner, the embodiments described herein can be used with any repeater analysis method or system in that the results of the transformed relative defect positions produced by the embodiments described herein can be input to any repeater analysis method or system. In addition, the substantially high accuracy relative defect positions produced by the embodiments described herein provide advantages for repeater analysis regardless of how the repeater analysis is performed.

In another embodiment, the one or more computer subsystems are configured for determining if the defects are caused on the wafer by the reticle used to print patterned features on the wafer based on the transformed swath coordinates for the defects. In one such embodiment, the reticle is an extreme ultraviolet (EUV) reticle. For example, the embodiments described herein can be used for print check for EUV mask monitoring, which is performed to detect repeaters periodically during wafer production. In other words, determining if the defects are caused on the wafer by the reticle may include performing repeater analysis as described above and then possibly examining the detected repeaters to determine if they correspond to some feature or defect on the reticle. As described further herein, the embodiments are particularly suitable for detection of repeating defects on wafers printed with multi-die reticles. In addition, the embodiments described herein are particularly suitable for detection of repeating defects on wafers caused by EUV reticles (that is, reticles designed for use in EUV lithography performed with EUV light). Because such reticles do not include protective pellicles, they are more susceptible to contamination that occurs during lithography processes. As such, these reticles tend to need to be examined at regular intervals to determine if they are still suitable for use in lithography processes. The embodiments described herein provide methods and systems that are particularly suitable for such reticle examination.

In an additional embodiment, the output for the first of the frames used in the aligning step is output for an alignment target in the first of the frames, the output for the corresponding others of the frames used in the aligning step is output for alignment sites in the corresponding others of the frames, the computer subsystem(s) are configured for selecting alignment targets in the frames in the first of the multiple swaths in the first of the multiple instances of the reticle, and selecting the alignment targets includes selecting at least one of the alignment targets in each of the frames in the first of the multiple swaths in the first of the multiple instances of the reticle. In other words, at least one alignment target may be selected in each of the frames in a swath in the reticle instance that will be used as the first reticle instance. Such alignment target selection may be performed for each swath that will be scanned on the wafer. In this manner, at least one alignment target may be selected in each of the frames in each of the swaths in the reticle instance that will be used as the first reticle instance.

Figure 5:
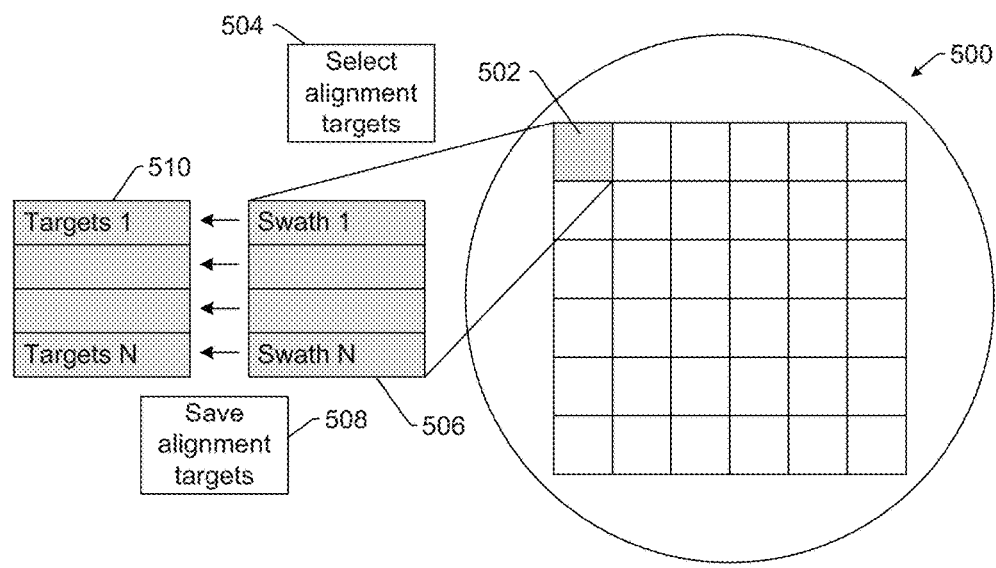
FIGS. 5 and 7 are schematic diagrams illustrating plan views of one example of instances of a reticle printed on a wafer and embodiments of selecting alignment targets in multiple swaths of one of the instances of the reticle for use in the embodiments described herein.

One such embodiment is shown in FIG. 5. In this embodiment, wafer 500 includes a number of reticle instances formed thereon including reticle instance 502, which may be used as the first of the multiple reticle instances in the embodiments described herein. In this embodiment, the computer subsystem(s) (not shown in FIG. 5) may perform select alignment targets step 504 in which alignment targets are selected from each swath in the first reticle instance. In particular, as shown in FIG. 5, an inspection subsystem configured as described herein may scan the first reticle instance in a number of swaths 506, including Swath 1 to Swath N. (Although the reticle instance is shown in FIG. 5 to be scanned in 4 swaths that divide the reticle instance vertically, reticle instances on the wafer described herein may be scanned in any suitable number of swaths, e.g., depending on the reticle and die configuration and the inspection subsystem configuration.) In this manner, the inspection subsystem may generate a number of swaths of inspection data or output for the wafer. Selecting the alignment targets in step 504 may include selecting alignment targets in at least one of the swaths (e.g., one swath, some (not all) of the swaths, or all of the swaths) depending on which one or more of the swaths will be examined for repeater defects. In particular, the alignment targets may be selected for each of the swaths for which repeater analysis will be performed. In addition, the alignment targets may be independently selected for each of the swaths. For example, the alignment targets in one of the swaths may be selected independently of the alignment targets in another (or all others) of the swaths.

The number of alignment targets that are selected in each swath may vary depending on the number of frames that are in the swaths. For example, one alignment target may be selected in each of the frames in whichever swath alignment targets are being selected. However, more than one target may also be selected in each frame. In general, the more alignment targets that are identified and selected for use in the embodiments described herein, the smaller the search range can be for repeater analysis. In addition, there is no guarantee that a suitable alignment target can be found in each frame. If no alignment target can be found for a particular frame, the normalized cross-correlation (or another alignment method described herein) on the entire frame may be used to align reticle instances or the information for a neighboring frame can be used to align reticle instances.

The alignment targets may include any suitable alignment targets and patterned features. A suitable alignment target may be an image pattern that satisfies certain criteria. For example, the alignment targets may be selected to include patterned features that are unique in one or more characteristics (e.g., shape, size, orientation, grey level change, etc.) within some area in a frame such that they can be used for alignment with relatively high confidence. The alignment targets may also preferably include features that render them suitable for alignment in two dimensions (x and y). In general, there are many ways to select suitable alignment targets within a frame of inspection output, and the alignment targets may be selected as described herein in any of those ways. It is noted, however, that the embodiments described herein are preferably performed without using design information (e.g., design data) for the wafer since the design information may not always be available (e.g., for intellectual property reasons). In this manner, the alignment target selection described herein may be performed using output (e.g., images) generated for the first reticle instance by the inspection subsystem (as opposed to using the design information to select the alignment targets). The embodiments described herein therefore provide the ability to achieve substantially high relative defect location accuracy for repeater analysis without design data.

As shown in FIG. 5, the computer subsystem(s) may be configured to perform save alignment targets step 508. The alignment targets that are selected may be saved (or stored in one or more of the computer-readable storage media described herein) in a number of different ways. Unless otherwise noted herein, the information for the alignment targets that have been selected may include any available information for the alignment targets, but will most likely include at a minimum the swath coordinates of the alignment targets, the frames in which the alignment targets are located, and the swaths in which the alignment targets are located. In this manner, the data for the alignment targets that is saved may look something like: Target(ID)=(alignment target swath coordinates, frame ID, swath ID, . . . ). As such, the computer subsystem(s) may generate stored target information 510. The stored target information may then be used as described further herein.

In another embodiment, the output for the first of the frames used in the aligning step is output for an alignment target in the first of the frames, the output for the corresponding others of the frames used in the aligning step is output for alignment sites in the corresponding others of the frames, and the computer subsystem(s) are configured for selecting alignment targets in the frames in the multiple swaths in the first of the multiple reticle instances, separating the selected alignment targets into groups based on the multiple swaths in which they are located such that each of the groups corresponds to fewer than all of the multiple swaths, and storing information for the selected alignment targets in the groups into different portions of the one or more computer subsystems based on which of the different portions of the one or more computer subsystems perform the detecting, aligning, determining, and applying for different ones of the groups, respectively. For example, the computer subsystem(s) may select the alignment targets as described further herein, and the computer subsystem(s) may save the targets into different image computer (IMC) nodes (not shown) included in the computer subsystem(s) and group the targets by swath. In particular, the targets may be stored in the IMC node that will process the swath of inspection output in which the targets are located. In this manner, the IMC nodes may store only the alignment targets that they will need for other steps described herein. Such grouping and storing is also not limited to just IMC nodes, but can be used for any of the other storage media described herein.

In this manner, as shown in FIG. 5, in one embodiment, the alignment targets selected from swath 1 may be stored as targets 1, which may be one group of the alignment targets, and alignment targets selected from swath N may be stored as targets N, which may be another group of alignment targets. Alignment target information may likewise be stored for any other swaths for which alignment targets were selected. As such, different groups of alignment targets may be generated by the computer subsystem(s), and each of the different groups may correspond to one of the different swaths. Each of the different groups of targets may then be stored in the different IMC node that will be using the different groups of targets. For example, the group of targets 1 may be stored in a first IMC node that will process the inspection output in swath 1, and the group of targets N may be stored in IMC node N that will process the inspection output in swath N. The information for the alignment targets in other groups may be stored in other IMC nodes in a similar manner.

In some embodiments, the output for the first of the frames used in the aligning step is output for an alignment target in the first of the frames, the output for the corresponding others of the frames used in the aligning step is output for alignment sites in the corresponding others of the frames, and the one or more computer subsystems are configured for selecting alignment targets in the frames in the multiple swaths in the first of the multiple instances of the reticle from the output generated for the wafer by the detector while the inspection subsystem directs the generated energy to the wafer and the detector detects the energy from the wafer for an inspection scan. In this manner, the alignment target selection, which may be performed as described further herein, may be performed during run time of a wafer inspection. The embodiments described herein therefore provide the ability to achieve substantially high relative defect location accuracy for repeater analysis without a setup scan (since a setup scan is not needed for alignment target selection). As such, the alignment target selection performed as described herein may be runtime target identification for relative alignment to a first inspected reticle instance. In other words, when inspecting the first reticle instance, alignment targets are selected from the first reticle instance. At least one target per frame can be selected. Such alignment target selection may be further performed as described herein.

Figure 6:
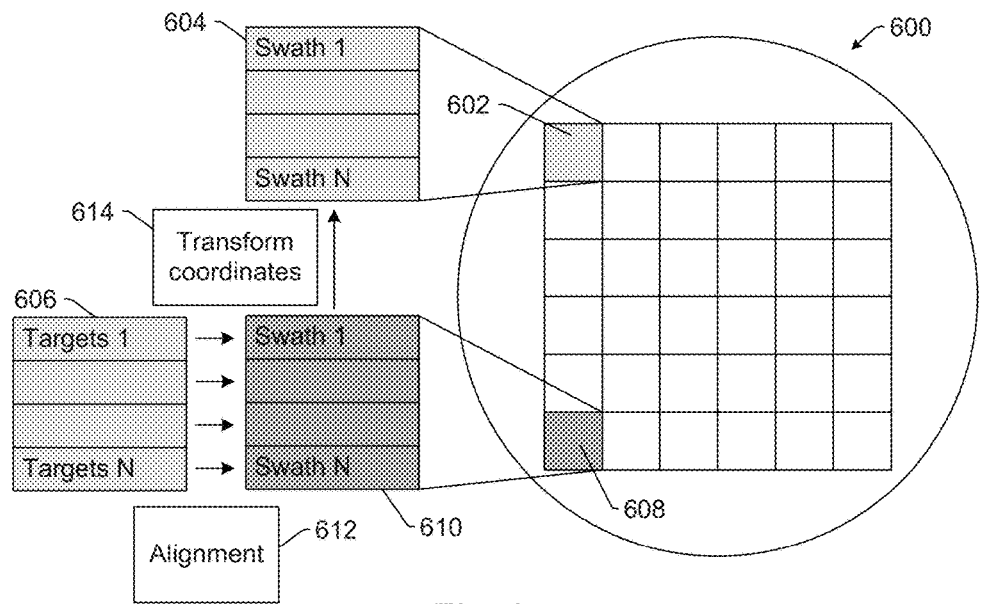
FIGS. 6 and 8 are schematic diagrams illustrating plan views of one example of instances of a reticle printed on a wafer and embodiments of transforming swath coordinates reported for defects detected on the wafer from swath coordinates in the instance of the reticle in which the defects were detected to swath coordinates of a first of the instances of the reticle printed on the wafer.

FIG. 6 shows a run time process that may be performed for any other inspected reticle instance after the alignment targets have been selected from the first reticle instance as described above. In FIG. 6, wafer 600 has a number of reticle instances formed thereon including reticle instance 602, which may be used as the first of the multiple reticle instances as described herein, and reticle instance 608, which may be another inspected reticle instance on the wafer. As described further above, first reticle instance 602 may be scanned thereby generating a number of swaths 604 of output from which targets 606 are selected as described herein. The targets in this embodiment may be selected during the runtime of the inspection process and may be stored as described further herein on corresponding IMC nodes (not shown) of the computer subsystem(s). For example, targets 1 may be stored on IMC node 1, . . . targets N may be stored on IMC node N, and so on. When other reticle instance 608 is then scanned thereby generating a number of swaths 610, the output for alignment targets 606 may be aligned to the output for alignment sites in corresponding frames and corresponding swaths 610 in alignment step 612. This alignment step may be performed as described further herein.

The results of the alignment step may then be used in transform coordinates step 614, which may include determining different swath coordinate offsets for each of the alignment sites, respectively, in the other reticle instances based on differences between swath coordinates of the output for the alignment sites and swath coordinates of the output for the alignment target aligned thereto in the aligning step and applying one of the different swath coordinate offsets to the swath coordinates reported for the defects detected on the wafer, where which of the different swath coordinate offsets is applied to the swath coordinates reported for the defects is determined based on the others of the multiple reticle instances in which the defects were detected. In this manner, the transform coordinates step 614 may transform swath coordinates reported for the defects from swath coordinates in reticle instance 608 to swath coordinates in first reticle instance 602. These steps may be performed for all of the reticle instances that are inspected on the wafer.

In this manner, the embodiments described herein may perform a reticle instance —swath coordinate transformation using runtime identified targets. As described further herein, when any other reticle instance is inspected, an offset between the swath coordinates of the first and the inspected reticle instances for each frame (and therefore each swath) may be determined by aligning targets of the first reticle instance to the inspected reticle instance. After any defect is detected, its location in the reticle instance-swath coordinates is transformed into the reticle instance-swath coordinates of the first reticle instance. In this way, positions of defects in all reticle instances are represented in terms of the swath coordinates of the first reticle instance.

In a further embodiment, the output for the first of the frames used in the aligning step is output for an alignment target in the first of the frames, the output for the corresponding others of the frames used in the aligning step is output for alignment sites in the corresponding others of the frames, and the computer subsystem(s) are configured for selecting alignment targets in the frames in the multiple swaths in one of the multiple instances of the reticle from output generated for the wafer by the detector in a setup scan of only the one of the multiple instances of the reticle performed before the detector of the inspection subsystem generates the output used to detect the defects on the wafer, generating a data structure containing information for the selected alignment targets, and storing the data structure in a non-transitory computer-readable storage medium. The "one reticle instance" or "setup reticle instance" used for setup can be any reticle instance on the wafer. In this manner, the alignment targets can be selected and stored in a setup scan of the wafer. For example, if throughput is relatively critical and target finding during inspection (runtime) is not acceptable, a setup scan can be used to select the targets offline. Such alignment target selection may be performed as shown in FIG. 5. However, unlike the alignment target selection during inspection runtime described above in which information for the selected alignment targets may be stored on the IMC nodes of the computer subsystem(s), when the alignment targets are selected during a setup scan, the information for the alignment targets may be stored to offline storage. The offline storage may be, for example, a database in a memory medium that is accessible to the computer subsystem(s) or one of the non-transitory computer-readable media described herein. In this manner, the embodiments described herein may include separate setup based alignment target identification and offline storage of targets. The alignment target selection performed during a setup phase of inspection may otherwise be performed as described herein. For example, in a setup scan, alignment targets may be selected from one reticle instance. At least one target per frame can be selected. The targets are then saved into an appropriate storage medium such as an offline database.

Alignment targets selected during a setup phase of inspection may be used for defect swath coordinate transformation as described further herein. For example, defect swath coordinate transformation using setup based targets may be performed as shown in FIG. 6. However, unlike the runtime alignment target selection described above, in this embodiment, targets 606 may be stored in offline storage instead of on the IMC nodes of the computer subsystem(s). During inspection, an offset between the swath coordinates of the setup reticle instance and the inspected reticle instance for each frame may be computed by aligning targets of the setup reticle instance to the image of the inspected reticle instance, which may be performed as described further herein. After any defect is detected, its location in the reticle instance-swath coordinates of the reticle instance in which it was detected may be transformed into the reticle instance-swath coordinates of the setup reticle instance as described further herein. In this way, defects in all other reticle instances may be represented in terms of the swath coordinates of the setup reticle instance.

In another embodiment, the output for the first of the frames used in the aligning step is output for an alignment target in the first of the frames, the output for the corresponding others of the frames used in the aligning step is output for alignment sites in the corresponding others of the frames, and the one or more computer subsystems are configured for selecting alignment targets in the frames in the multiple swaths in one of the multiple instances of the reticle from output generated for the wafer by the detector in a setup scan of only the one of the multiple instances of the reticle performed before the detector of the inspection subsystem generates the output used to detect the defects on the wafer, generating a data structure containing only location information for the selected alignment targets, and storing the data structure in a non-transitory computer-readable storage medium. In this manner, the alignment targets can be selected and their locations can be stored in a setup scan of the wafer. Only the target locations can be saved during setup to reduce the database (or other data structure) size. The embodiments described herein may, therefore, be configured for separate setup based alignment target identification and offline storage of target locations. In a setup scan, alignment targets are selected from "one reticle instance" or the "setup reticle instance." At least one target per frame can be selected. The target location information may then be stored into an offline database or any other suitable storage medium.

Figure 7:
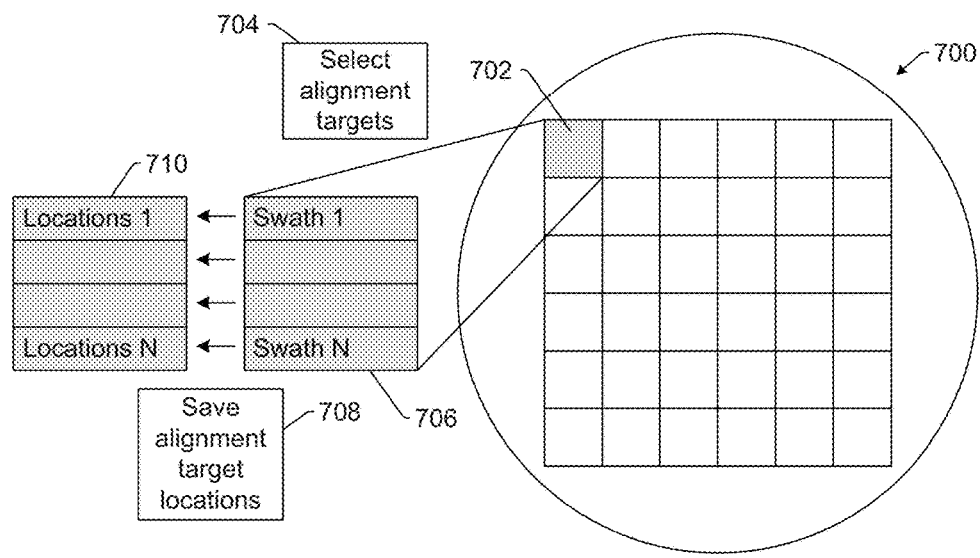

One such embodiment is shown in FIG. 7. Any reticle instance can be selected as the setup reticle instance. In FIG. 7, the first reticle instance is selected as the setup reticle instance. In this embodiment, wafer 700 may include a number of reticle instances formed thereon including reticle instance 702, which may be used as the one of the multiple reticle instances in the embodiments described herein. In this embodiment, the computer subsystem(s) (not shown in FIG. 7) may perform select alignment targets step 704 in which alignment targets are selected from each swath in the setup reticle instance. In particular, as shown in FIG. 7, an inspection subsystem configured as described herein may scan the setup reticle instance in a number of swaths 706, including Swath 1 to Swath N. In this manner, the inspection subsystem may generate a number of swaths of inspection data or output for the wafer. Selecting the alignment targets in step 704 may be performed as described herein. The alignment targets may be configured as described further herein.

As shown in FIG. 7, the computer subsystem(s) may be configured to perform save alignment target locations step 708. The locations of the alignment targets that are selected may be saved (or stored in one or more of the computer-readable storage media described herein) in a number of different ways. Unless otherwise noted herein, the location information for the alignment targets that have been selected may include any available location information for the alignment targets, but will most likely include at a minimum the swath coordinates of the alignment targets, the frame in which the alignment targets are located, and the swath in which the alignment targets are located. In this manner, the data for the alignment targets that is saved may look something like: Target(ID)=(alignment target swath coordinates, frame ID, swath ID, . . . ). As such, the computer subsystem(s) may generate stored target location information 710, which in this case includes only location information. In particular, the alignment target location information that is stored for the alignment targets in Swath 1 may include Locations 1, . . . the alignment target location information that is stored for alignment targets in Swath N may include Locations N, etc. The stored target location information may then be used as described further herein.

Figure 8:
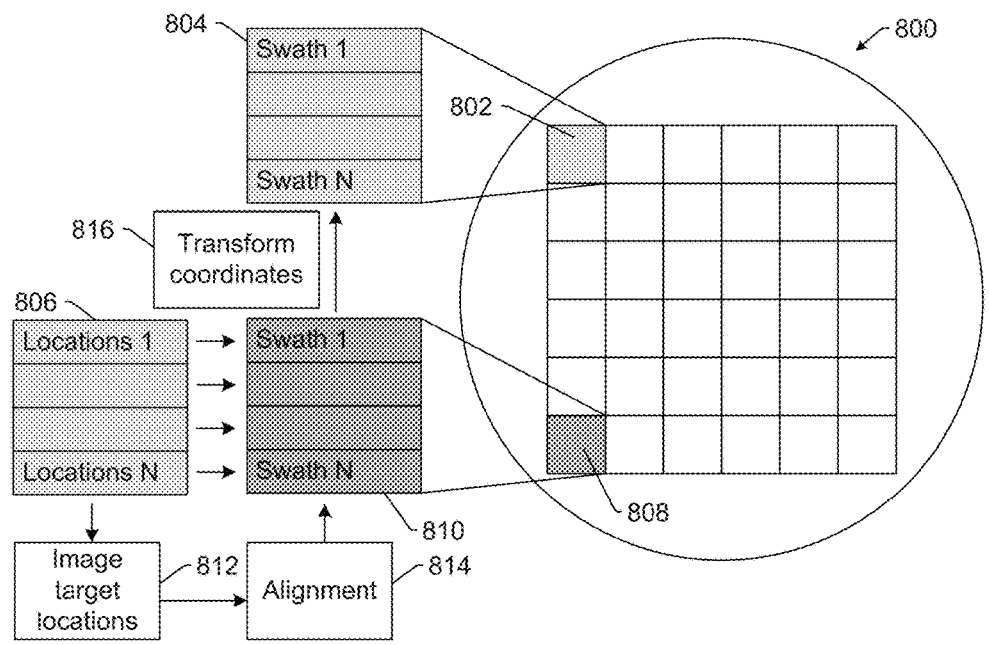

In one such embodiment, the one or more computer subsystems are configured for acquiring the output generated by the detector for the selected alignment targets in the multiple instances of the reticle during inspection of the wafer based on only the location information. In this manner, targets (e.g., target images) can be created during inspection based on the target locations. One such embodiment is shown in FIG. 8. In this figure, wafer 800 includes a number of reticle instances including reticle instance 802, which is used as the setup reticle instance in this embodiment, and reticle instance 808, which is another inspected reticle instance in this embodiment. As described further herein, in a setup scan, reticle instance 802 may be scanned to thereby generate a number of swaths 804 of output for the reticle instance. That output may then be used as described further herein to select alignment targets, for which only the location information may be stored as stored location information 806.

In some such embodiments, the one or more computer subsystems are configured for separating the selected alignment targets into groups based on the multiple swaths in which they are located such that each of the groups correspond to fewer than all of the multiple swaths and storing the acquired output for the selected alignment targets in the groups into different portions of the one or more computer subsystems based on which of the different portions of the one or more computer subsystems perform the detecting, the aligning, the determining, and the applying for different ones of the groups, respectively. For example, the location information for the selected alignment targets may be stored in offline storage based on the swath in which the alignment targets are located. In this manner, the alignment targets may be grouped by swath and then the location information for different groups of the alignment targets may be stored into different portions of the computer subsystem(s) (e.g., based on which portion of the computer subsystem(s) will process the output generated for each swath). The location information for the alignment targets may otherwise be stored as described further herein.

During inspection of the wafer, alignment target locations identified in reticle instance 802 may be scanned based on stored location information 806, as shown in image target locations step 812. In this manner, image target locations step 812 may include grabbing and storing target patches on the first reticle instance of multiple inspected reticle instances. Reticle instance 808 may also be scanned during inspection of the wafer to thereby generate a number of swaths 810 for that reticle instance. Alignment step 814 may then be performed as described further herein using the stored alignment target patches grabbed in step 812 and the output generated for reticle instance 808 at the corresponding alignment sites in the corresponding frames and swaths. The results of the alignment step may then be used for transform coordinates step 816, which may be performed as described further herein, to thereby transform swath coordinates of defects detected in reticle instance 808 to swath coordinates in reticle instance 802.

The embodiments described herein may therefore be configured for reticle instance-swath coordinate transformation using setup-based target locations. During inspection, target patches (i.e., patch images, which are relatively small images generated at specific locations) may be grabbed and stored on image computer nodes based on target locations. During target patch grabbing, only the locations of the alignment targets may be scanned for image grabbing. However, during target patch grabbing, the entirety of the first reticle instance that is to be inspected may be scanned to thereby generate both images of the stored alignment target locations as well as output that will be used to detect defects in the first reticle instance. An offset between the swath coordinates of the first reticle instance and the inspected reticle instance for each frame may be determined by aligning targets of the grabbed images to the image of the inspected reticle instance. After any defect is detected, its location in the reticle instance-swath coordinates of the reticle instance in which it is detected is transformed into the reticle instance-swath coordinates of the first reticle instance as described further herein. In this way, defects in all other reticle instances can be represented in terms of the swath coordinates of the first reticle instance.

In some embodiments, the one or more computer subsystems are not configured to determine positions of the defects relative to the wafer. For example, none of the embodiments described herein include or require determining positions of the defects relative to a reference point on a wafer or other wafer. Instead, the only positions of the defects that are determined in (or by) the embodiments described herein are swath coordinates reported by the defect detecting step and the transformed swath coordinates determined by the applying step. Since the embodiments described herein were created specifically to address issues in repeater analysis caused by relative defect location accuracy, which is improved by the embodiments described herein by transforming swath coordinates of defects in one reticle instance to swath coordinates in another reticle instance, no other (e.g., wafer relative) defects positions need to be determined by the embodiments described herein.

In another embodiment, the one or more computer subsystems are configured for repeating the aligning, the determining, and the applying steps for others of the frames in the multiple swaths in the first of the multiple instances of the reticle. For example, although some embodiments are described herein with respect to a first frame and a first swath in the first reticle instance, the embodiments may perform the aligning, determining, and applying for other frames in other swaths in the first reticle instance. In other words, the embodiments described herein may perform the aligning, determining, and applying steps for one, some (e.g., two or more), or all of the frames being inspected on a wafer. In addition, the embodiments described herein may be performed for one, some (e.g., two or more), or all of the defects detected on a wafer regardless of the positions reported for the defects.

The embodiments described herein have a number of advantages over other methods and systems for determining defect positions. For example, the embodiments described herein transform defect locations from all reticle instances to common coordinates during inspection and significantly increase relative defect location accuracy. In an additional example, the swath-to-swath (reticle instance-to-reticle instance) offset is removed from the defect locations. In particular, after swath offsets are measured or determined, defect locations can be transformed from a swath in one reticle instance to the corresponding swath in the first reticle instance. After transformation, the offsets between swaths and reticle instances are therefore removed. In this manner, the variation (about 0.1 pixel to about 1 pixel) of defect locations relative to one reticle instance-swath is much smaller than the variation (about 10 pixels) of defect locations across multiple swaths. In another example, for repeater analysis, the search area reduction provided by the embodiments described herein may be 100× to 10,000× and search range (repeater tolerance) reduction provided by the embodiments described herein is about 10× to about 100×. In an additional example, the embodiments described herein potentially reduce false repeaters significantly. In other words, the embodiments described herein can reduce the false repeater count for repeater analysis. Furthermore, the embodiments described herein are particularly advantageous for non-context based inspection (non-CBI) and multi-die reticle use cases unlike other defect position determination methods like aligning inspection output to design data and standard reference die (SRD) methods. Moreover, unlike previously used defect position determination methods and systems, the embodiments described herein do not necessarily require a setup scan and are easier to use.

More specifically, with respect to previously used SRD methods, the embodiments described herein and those previously used methods may be capable of the same relative defect location accuracy. The embodiments described herein and SRD methods may also both align targets to inspection images during runtime, and some of the embodiments described herein and SRD methods both save target locations into a database. However, unlike SRD methods and systems, the embodiments described herein do not generate a golden reference image offline (of a whole die) that is used during inspection. In addition, unlike SRD methods and systems, some of the embodiments described herein do not necessarily require a setup scan. The embodiments described herein are therefore simpler for development and ease of use than SRD methods and systems. Furthermore, SRD methods and systems and the embodiments described herein are suitable for different use cases. In particular, SRD methods and systems are suitable for single die reticle use cases, while the embodiments described herein are particularly suitable for multi-die reticles without design information.

With respect to previously used CBI methods, the embodiments described herein and those previously used methods may both align targets to an inspection image during run time. In addition, like CBI methods, some of the embodiments described herein may save targets into a database. However, unlike previously used CBI methods and systems, the embodiments described herein do not require design information and no inspection output to design data alignment is required. In addition, unlike CBI methods and systems, some of the embodiments described herein do not necessarily require a setup scan. Additionally, unlike CBI methods and systems, some of the embodiments described herein do not save alignment target output (e.g., images) and instead only save alignment target location information. Furthermore, the embodiments described herein provide potentially better relative defect location accuracy than previously used CBI methods and systems. Moreover, CBI methods and systems and the embodiments described herein are suitable for different use cases. In particular, CBI methods and systems are suitable for multi-die reticle with design information use cases, while the embodiments described herein are particularly suitable for multi-die reticles without design information.

The embodiments described herein also provide a simpler way to achieve substantially high defect location accuracy for repeater analysis without sacrificing performance. The implementation is simpler and it is simpler for users to use than other existing approaches. Repeater analysis is substantially important to reduce nuisance rate for the EUV print check use case, which will be very likely adopted by advanced semiconductor manufacturers in the next couple of years.

Each of the embodiments described herein may be further configured as described herein. For example, two or more of the embodiments described herein may be combined into one single embodiment.

Another embodiment relates to a computer-implemented method for transforming positions of defects detected on a wafer. The method includes detecting defects on a wafer by applying a defect detection method to output generated for the wafer by a detector of an inspection subsystem, which is configured as described further herein. Positions of the defects are reported by the defect detection method in swath coordinates. The output generated by the detector of the inspection subsystem includes multiple swaths of frames of output for each of multiple dies on the wafer, and each of multiple instances of a reticle printed on the wafer includes at least two instances of the multiple dies.

The method also includes aligning the output for a first of the frames in a first of the multiple swaths in a first of the multiple dies in a first of the multiple instances of the reticle printed on the wafer to the output for corresponding others of the frames in corresponding others of the multiple swaths in corresponding others of the multiple dies in others of the multiple instances of the reticle printed on the wafer. In addition, the method includes determining different swath coordinate offsets for each of the frames, respectively, in the others of the multiple instances of the reticle based on differences between swath coordinates of the output for the frames and swath coordinates of the output for the first of the frames aligned thereto in the aligning step.

The method further includes applying one of the different swath coordinate offsets to the swath coordinates reported for the defects detected on the wafer, where which of the different swath coordinate offsets is applied to the swath coordinates reported for the defects is determined based on the others of the multiple instances of the reticle in which the defects were detected, thereby transforming the swath coordinates reported for the defects from swath coordinates in the others of the multiple instances of the reticle to swath coordinates in the first of the multiple instances of the reticle. The detecting, the aligning, the determining, and the applying are performed by one or more computer subsystems coupled to the inspection subsystem.

Each of the steps of the method may be performed as described further herein. The method may also include any other step(s) that can be performed by the inspection subsystem and/or computer subsystem(s) or system(s) described herein. The steps of the method are performed by one or more computer subsystems, which may be configured according to any of the embodiments described herein. In addition, the method described above may be performed by any of the system embodiments described herein.

Figure 9:
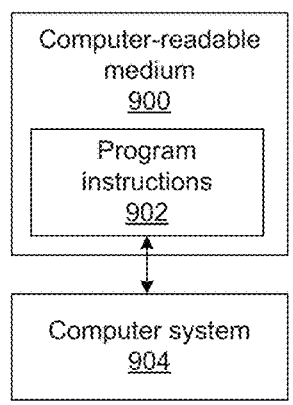
FIG. 9 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for transforming positions of defects detected on a wafer. One such embodiment is shown in FIG. 9. In particular, as shown in FIG. 9, non-transitory computer-readable medium 900 includes program instructions 902 executable on computer system 904. The computer-implemented method may include any step(s) of any method(s) described herein.

Program instructions 902 implementing methods such as those described herein may be stored on computer-readable medium 900. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, Java-Beans, Microsoft Foundation Classes ("MFC"), SSE (Streaming SIMD Extension) or other technologies or methodologies, as desired.

Computer system 904 may be configured according to any of the embodiments described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, the one or more computer subsystem(s) may output information for the defects identified as repeaters to a reticle repair system, and the reticle repair system may use the information for the defects identified as repeaters to perform a repair process on the reticle to thereby eliminate the defects on the reticle.

Further modifications and alternative embodiments of various aspects of the invention will be apparent to those skilled in the art in view of this description. For example, methods and systems for transforming positions of defects detected on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to transform positions of defects detected on a wafer, comprising:
   an inspection subsystem comprising at least an energy source and a detector, wherein the energy source is configured to generate energy that is directed to a wafer, wherein the detector is configured to detect energy from the wafer and to generate output responsive to the detected energy, wherein the output comprises multiple swaths of frames of output for each of multiple dies on the wafer, and wherein each of multiple instances of a reticle printed on the wafer comprises at least two instances of the multiple dies; and
   one or more computer subsystems configured for:
      detecting defects on the wafer by applying a defect detection method to the output generated by the detector, wherein positions of the defects are reported by the defect detection method in swath coordinates;
      aligning the output for a first of the frames in a first of the multiple swaths in a first of the multiple dies in a first of the multiple instances of the reticle printed on the wafer to the output for corresponding others of the frames in corresponding others of the multiple swaths in corresponding others of the multiple dies in others of the multiple instances of the reticle printed on the wafer,
      determining different swath coordinate offsets for each of the frames, respectively, in the others of the multiple instances of the reticle based on differences between swath coordinates of the output for the frames and swath coordinates of the output for the first of the frames aligned thereto in the aligning step; and
      applying one of the different swath coordinate offsets to the swath coordinates reported for the defects detected on the wafer, wherein which of the different swath coordinate offsets is applied to the swath coordinates reported for the defects is determined based on the others of the multiple instances of the reticle in which the defects were detected, thereby transforming the swath coordinates reported for the defects from swath coordinates in the others of the multiple instances of the reticle to swath coordinates in the first of the multiple instances of the reticle.

2. The system of claim 1, wherein the one or more computer subsystems are further configured for performing said aligning, said determining, and said applying without design information for devices being formed on the wafer.

3. The system of claim 1, wherein the one or more computer subsystems are not configured to perform any steps using design information for devices being formed on the wafer.

4. The system of claim 1, wherein the one or more computer subsystems are further configured for determining if the defects are repeater defects based on the transformed swath coordinates for the defects.

5. The system of claim 1, wherein the one or more computer subsystems are further configured for determining if the defects are caused on the wafer by the reticle used to print patterned features on the wafer based on the transformed swath coordinates for the defects.

6. The system of claim 1, wherein the one or more computer subsystems are further configured for determining if the defects are caused on the wafer by the reticle used to print patterned features on the wafer based on the transformed swath coordinates for the defects, and wherein the reticle is an extreme ultraviolet reticle.

7. The system of claim 1, wherein the output for the first of the frames used in the aligning step is output for an alignment target in the first of the frames, wherein the output for the corresponding others of the frames used in the aligning step is output for alignment sites in the corresponding others of the frames, wherein the one or more computer subsystems are further configured for selecting alignment targets in the frames in the first of the multiple swaths in the first of the multiple instances of the reticle, and wherein said selecting the alignment targets comprises selecting at least one of the alignment targets in each of the frames in the first of the multiple swaths in the first of the multiple instances of the reticle.

8. The system of claim 1, wherein the output for the first of the frames used in the aligning step is output for an alignment target in the first of the frames, wherein the output for the corresponding others of the frames used in the aligning step is output for alignment sites in the corresponding others of the frames, and wherein the one or more computer subsystems are further configured for selecting alignment targets in the frames in the multiple swaths in the first of the multiple instances of the reticle, separating the selected alignment targets into groups based on the multiple swaths in which they are located such that each of the groups corresponds to fewer than all of the multiple swaths, and storing information for the selected alignment targets in the groups into different portions of the one or more computer subsystems based on which of the different portions of the one or more computer subsystems perform said detecting, said aligning, said determining, and said applying for different ones of the groups, respectively.

9. The system of claim 1, wherein the output for the first of the frames used in the aligning step is output for an alignment target in the first of the frames, wherein the output for the corresponding others of the frames used in the aligning step is output for alignment sites in the corresponding others of the frames, and wherein the one or more computer subsystems are further configured for selecting alignment targets in the frames in the multiple swaths in the first of the multiple instances of the reticle from the output generated for the wafer by the detector while the inspection subsystem directs the generated energy to the wafer and the detector detects the energy from the wafer for an inspection scan.

10. The system of claim 1, wherein the output for the first of the frames used in the aligning step is output for an alignment target in the first of the frames, wherein the output for the corresponding others of the frames used in the aligning step is output for alignment sites in the corresponding others of the frames, and wherein the one or more computer subsystems are further configured for selecting alignment targets in the frames in the multiple swaths in one of the multiple instances of the reticle from output generated for the wafer by the detector in a setup scan of only the one of the multiple instances of the reticle performed before the detector of the inspection subsystem generates the output used to detect the defects on the wafer, generating a data structure containing information for the selected alignment targets, and storing the data structure in a non-transitory computer-readable storage medium.

11. The system of claim 1, wherein the output for the first of the frames used in the aligning step is output for an alignment target in the first of the frames, wherein the output for the corresponding others of the frames used in the aligning step is output for alignment sites in the corresponding others of the frames, and wherein the one or more computer subsystems are further configured for selecting alignment targets in the frames in the multiple swaths in one of the multiple instances of the reticle from output generated for the wafer by the detector in a setup scan of only the one of the multiple instances of the reticle performed before the detector of the inspection subsystem generates the output used to detect the defects on the wafer, generating a data structure containing only location information for the selected alignment targets, and storing the data structure in a non-transitory computer-readable storage medium.

12. The system of claim 11, wherein the one or more computer subsystems are further configured for acquiring the output generated by the detector for the selected alignment targets in the one of the multiple instances of the reticle during inspection of the wafer based on only the location information.

13. The system of claim 12, wherein the one or more computer subsystems are further configured for separating the selected alignment targets into groups based on the multiple swaths in which they are located such that each of the groups corresponds to fewer than all of the multiple swaths and storing the acquired output for the selected alignment targets in the groups into different portions of the one or more computer subsystems based on which of the different portions of the one or more computer subsystems perform said detecting, said aligning, said determining, and said applying for different ones of the groups, respectively.

14. The system of claim 1, wherein said aligning comprises target-based alignment of the output for the first of the frames to the output for the corresponding others of the frames.

15. The system of claim 1, wherein said aligning comprises feature-based alignment of the output for the first of the frames to the output for the corresponding others of the frames.

16. The system of claim 1, wherein said aligning comprises normalized cross correlation-based alignment of the output for the first of the frames to the output for the corresponding others of the frames.

17. The system of claim 1, wherein said aligning comprises Fast Fourier transform-based alignment of the output for the first of the frames to the output for the corresponding others of the frames.

18. The system of claim 1, wherein said aligning comprises sum of squared difference-based alignment of the output for the first of the frames to the output for the corresponding others of the frames.

19. The system of claim 1, wherein the one or more computer subsystems are not configured to determine positions of the defects relative to the wafer.

20. The system of claim 1, wherein the one or more computer subsystems are further configured for repeating said aligning, said determining, and said applying for others of the frames in the multiple swaths in the first of the multiple instances of the reticle.

21. The system of claim 1, wherein the energy directed to the wafer comprises light, and wherein the energy detected from the wafer comprises light.

22. The system of claim 1, wherein the energy directed to the wafer comprises electrons, and wherein the energy detected from the wafer comprises electrons.

23. A non-transitory computer-readable medium, storing program instructions executable on a computer system for performing a computer-implemented method for transforming positions of defects detected on a wafer, wherein the computer-implemented method comprises:

detecting defects on a wafer by applying a defect detection method to output generated for the wafer by a detector of an inspection subsystem, wherein positions of the defects are reported by the defect detection method in swath coordinates, wherein the inspection subsystem comprises at least an energy source and the detector, wherein the energy source is configured to generate energy that is directed to the wafer, wherein the detector is configured to detect energy from the wafer and to generate the output responsive to the detected energy, and wherein the output comprises multiple swaths of frames of output for each of multiple dies on the wafer, and wherein each of multiple instances of a reticle printed on the wafer comprises at least two instances of the multiple dies;

aligning the output for a first of the frames in a first of the multiple swaths in a first of the multiple dies in a first of the multiple instances of the reticle printed on the wafer to the output for corresponding others of the frames in corresponding others of the multiple swaths in corresponding others of the multiple dies in others of the multiple instances of the reticle printed on the wafer;

determining different swath coordinate offsets for each of the frames, respectively, in the others of the multiple instances of the reticle based on differences between swath coordinates of the output for the frames and swath coordinates of the output for the first of the frames aligned thereto in the aligning step; and applying one of the different swath coordinate offsets to the swath coordinates reported for the defects detected on the wafer, wherein which of the different swath coordinate offsets is applied to the swath coordinates reported for the defects is determined based on the others of the multiple instances of the reticle in which the defects were detected, thereby transforming the swath coordinates reported for the defects from swath coordinates in the others of the multiple instances of the reticle to swath coordinates in the first of the multiple instances of the reticle.

24. A computer-implemented method for transforming positions of defects detected on a wafer, comprising:

detecting defects on a wafer by applying a defect detection method to output generated for the wafer by a detector of an inspection subsystem, wherein positions of the defects are reported by the defect detection method in swath coordinates, wherein the inspection subsystem comprises at least an energy source and the detector, wherein the energy source is configured to generate energy that is directed to the wafer, wherein the detector is configured to detect energy from the wafer and to generate the output responsive to the detected energy, and wherein the output comprises multiple swaths of frames of output for each of multiple dies on the wafer, and wherein each of multiple instances of a reticle printed on the wafer comprises at least two instances of the multiple dies;

aligning the output for a first of the frames in a first of the multiple swaths in a first of the multiple dies in a first of the multiple instances of the reticle printed on the wafer to the output for corresponding others of the frames in corresponding others of the multiple swaths in corresponding others of the multiple dies in others of the multiple instances of the reticle printed on the wafer;

determining different swath coordinate offsets for each of the frames, respectively, in the others of the multiple instances of the reticle based on differences between swath coordinates of the output for the frames and swath coordinates of the output for the first of the frames aligned thereto in the aligning step; and applying one of the different swath coordinate offsets to the swath coordinates reported for the defects detected on the wafer, wherein which of the different swath coordinate offsets is applied to the swath coordinates reported for the defects is determined based on the others of the multiple instances of the reticle in which the defects were detected, thereby transforming the swath coordinates reported for the defects from swath coordinates in the others of the multiple instances of the reticle to swath coordinates in the first of the multiple instances of the reticle, and wherein said detecting, said aligning, said determining, and said applying are performed by one or more computer subsystems coupled to the inspection subsystem.

* * * * *